(12) United States Patent
Krafczyk et al.

(10) Patent No.: US 6,380,413 B2
(45) Date of Patent: Apr. 30, 2002

(54) PROCESS FOR THE PREPARATION OF YELLOW BIS (3-[TRIETHOXYSILYL] PROPYL) TETRASULFANE

(75) Inventors: Roland Krafczyk, Rheinfelden; Ulrich Deschler, Sailaut; Rudolf Michel, Freigericht, all of (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/852,050

(22) Filed: May 10, 2001

(30) Foreign Application Priority Data

May 13, 2000 (DE) .......................................... 100 24 037

(51) Int. Cl.[7] .................................................. C07F 7/08
(52) U.S. Cl. ....................................................... 556/427
(58) Field of Search .......................................... 556/427

(56) References Cited

U.S. PATENT DOCUMENTS

| 6,046,349 | A | * | 4/2000 | Batz-sohn et al. | 556/427 |
| 6,172,251 | B1 | * | 1/2001 | Parker | 556/427 |
| 6,194,595 | B1 | * | 2/2001 | Michel et al. | 556/427 |
| 6,274,755 | B1 | * | 8/2001 | Munzenberg et al. | 556/427 |
| 6,294,683 | B1 | * | 9/2001 | Johnson et al. | 556/427 |

* cited by examiner

*Primary Examiner*—Paul F. Shaver
(74) *Attorney, Agent, or Firm*—Pillsbury Winthrop LLP

(57) ABSTRACT

Process for the preparation of yellow bis(3-[triethoxysilyl]propyl)tetrasulfane having an iodine colour value of $\leq 10$ mg of iodine/100 ml, in which process a small amount of chloropropyltrichlorosilane is added to neutral chloropropyltriethoxysilane and reaction with sodium polysulfide or with $Na_2S$ and sulfur in ethanol is then carried out.

3 Claims, 2 Drawing Sheets

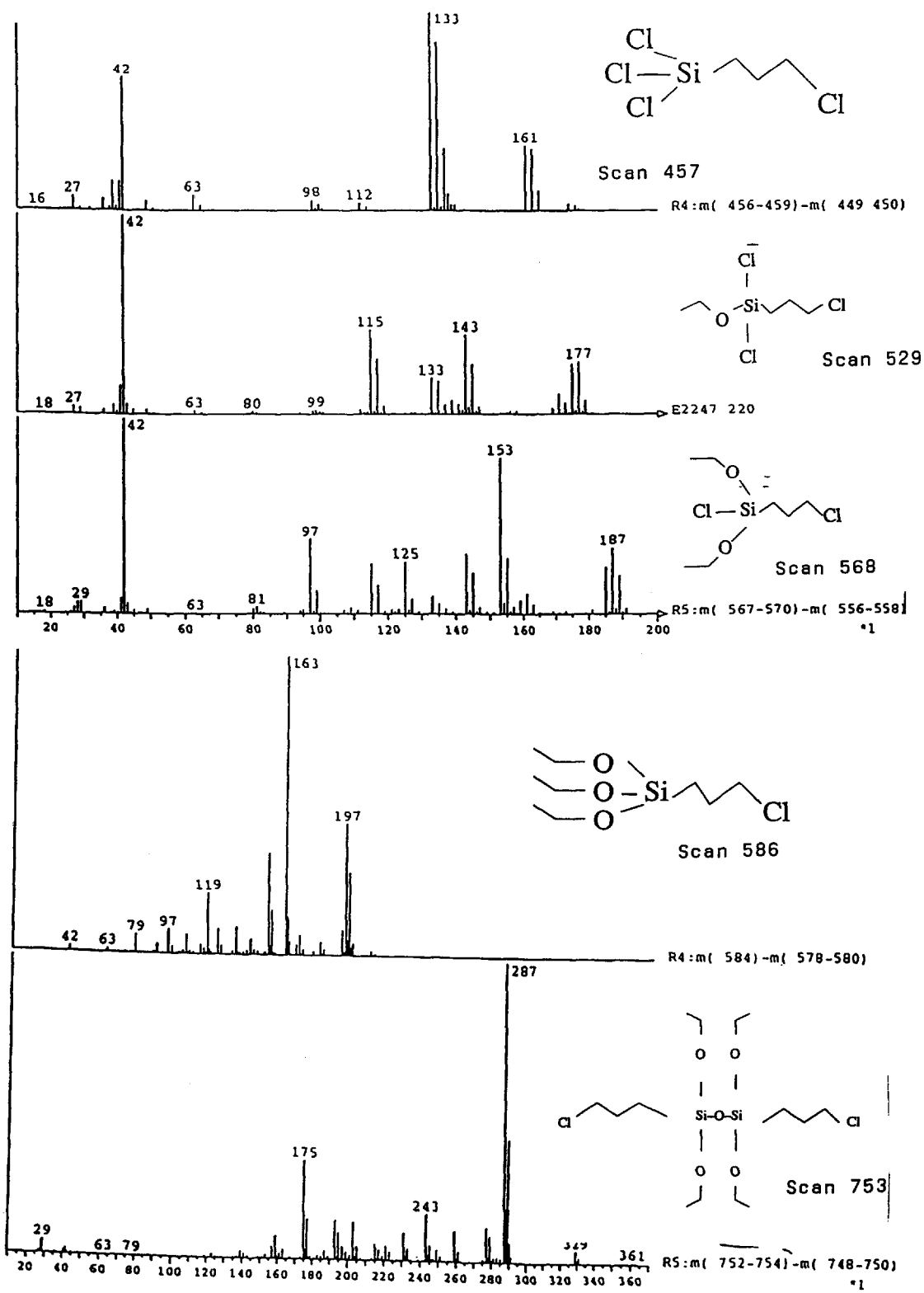
Figur 1

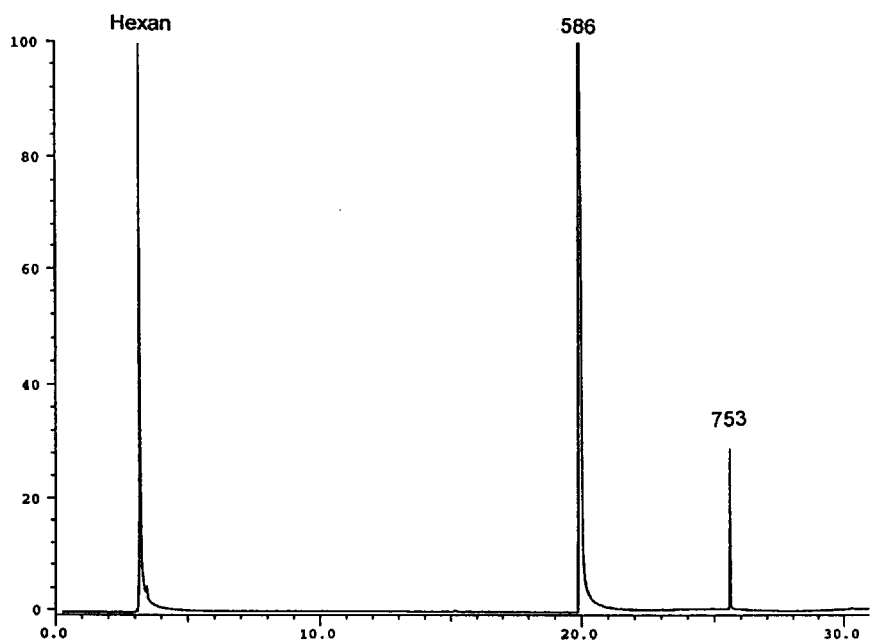
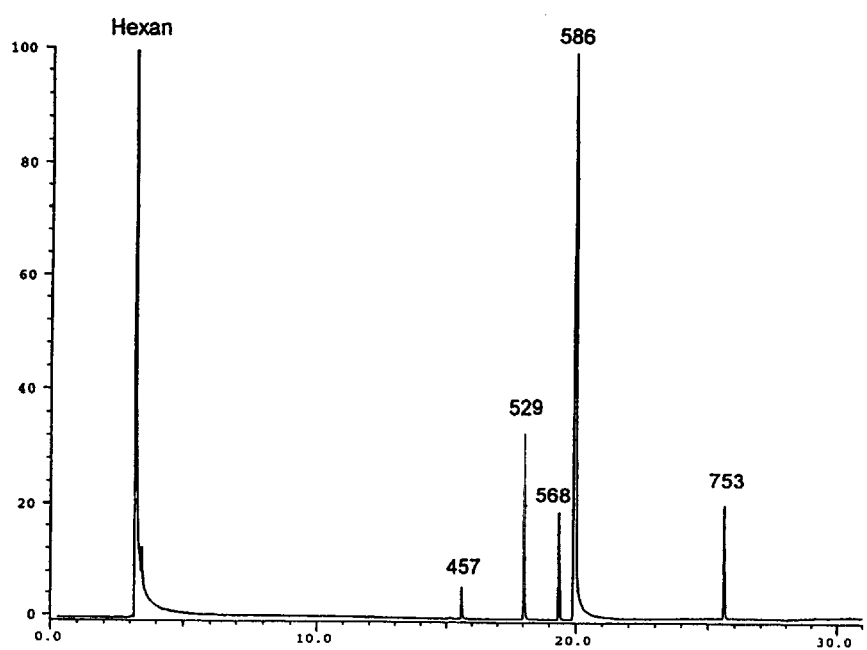
Figur 2

PROCESS FOR THE PREPARATION OF YELLOW BIS (3-[TRIETHOXYSILYL] PROPYL) TETRASULFANE

CROSS REFERENCE TO RELATED APPLICATIONS

The present application claims priority under 35 U.S.C. §119 to German application no. 100 24 037.2, filed on May 13, 2000.

The invention relates to the preparation of yellow bis(3-[triethoxysilyl]propyl)tetrasulfane.

From DE 21 41 159 there is known the preparation of bis(3-[triethoxysilyl]propyl)tetrasulfane (Si 69) by reaction of chloropropyltriethoxysilane with sodium polysulfide (NPS). The chloropropyltriethoxysilane that is used can be prepared by ethanolysis of chloropropyltrichlorosilane. Ethanolysis according to known processes, as described in DE 20 61 189 and DE 32 36 628, yields a completely converted product having only a very low content of chloropropylmonochlorodiethoxysilane. Such completely converted chloropropyltriethoxysilane is referred to as "neutral" hereinbelow.

If neutral chloropropyltriethoxysilane is reacted according to the process described in DE 21 41 159 with sodium polysulfide or with $Na_2S$ and sulfur to prepare bis(3-[triethoxysilyl]propyl)tetrasulfane, then a product that is dark yellow to red in colour (iodine colour value $\geq 20$ mg of iodine/100 ml) is obtained. There has been introduced onto the market, however, a light-yellow product that is not obtainable from neutral chloropropyltriethoxysilane. In order to obtain light-yellow bis(3-[triethoxysilyl]propyl)tetrasulfane (iodine colour value $\leq 10$ mg of iodine/100 ml), a so-called residual acid content in the form of chloropropylmonochlorodiethoxysilane must be present in the chloropropyltriethoxysilane. That can be achieved by not bringing the ethanolysis reaction completely to an end. In operational practice, however, such a measure requires a not inconsiderable additional expense, in particular because the residual acid content must be kept within a very narrow range, that is to say the reaction must be terminated very specifically at a particular point shortly before conversion is complete.

Acidification of neutral chloropropyltriethoxysilane with alcoholic hydrochloric acid before the reaction with the mentioned sulfurising agents also yields bis(3-[triethoxysilyl]propyl)tetrasulfane that is not light-yellow but likewise dark yellow to red in colour.

The disadvantage of such known processes is that they yield a product that is dark yellow to red in colour.

The object of the invention is to provide an alternative process by means of which a yellow bis(3-[triethoxysilyl]propyl)tetrasulfane is obtained.

The invention provides a process for the preparation of yellow bis(3-[triethoxysilyl]propyl)tetrasulfane having an iodine colour value of $\leq 10$ mg of iodine/100 ml, preferably from 5 to 7 mg of iodine/100 ml, which process is characterised in that chloropropyltrichlorosilane is added to neutral chloropropyltriethoxysilane and reaction with sodium polysulfide or with $Na_2S$ and sulfur in ethanol is then carried out.

The addition of small amounts of chloropropyltrichlorosilane to neutral chloropropyltriethoxysilane can lead to the formation of small amounts of chloropropylmonochlorodiethoxysilane and chloropropyldichloromonoethoxysilane (1).

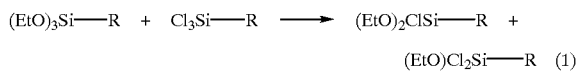

wherein R = $(CH_2)_3Cl$

The formation of chloropropylmonochlorodiethoxysilane and chloropropyldichloromonoethoxysilane, even in the absence of a solvent such as, for example, ethanol, can be confirmed by GC-MS investigations.

That process has the advantage that the ethanolysis reaction does not have to be terminated very specifically at a particular point shortly before conversion is complete, but can be carried out to complete conversion to neutral chloropropyltriethoxysilane. The small amount of chloropropylmonochlorodiethoxysilane that is required for the preparation of light-yellow bis(3-[triethoxysilyl]propyl)tetrasulfane can be obtained in a simple manner by adding chloropropyltrichlorosilane to neutral chloropropyltriethoxysilane.

The metering sequence is not critical. It is possible to add chloropropyltrichlorosilane to a solution of neutral chloropropyltriethoxysilane and ethanol, or chloropropyltrichlorosilane may be added to neutral chloropropyltriethoxysilane, followed by ethanol.

Chloropropyltrichlorosilane may be added in amounts of from 0.1 to 20 wt. %, preferably from 0.5 to 5 wt. %, particularly preferably from 0.8 to 1.2 wt. %, based on chloropropyltriethoxysilane.

The reaction mixture may be heated before the addition of sodium polysulfide or $Na_2S$ and sulfur, preferably to temperatures of from 20 to 90° C.

Bis(3-[triethoxysilyl]propyl)tetrasulfane prepared by the process according to the invention has an iodine colour value of $\leq 10$ mg of iodine/100 ml.

EXAMPLES

Example 1

2.4 g of chloropropyltrichlorosilane are added dropwise at room temperature to a solution of 240.8 g of chloropropyltriethoxysilane (neutral) in 200 ml of ethanol. Boiling at reflux is then carried out for one hour at 82° C., with stirring. After cooling to 60° C., 87.1 g of sodium polysulfide are added and the reaction mixture is boiled at reflux for 1.5 hours at 82° C., with stirring. After cooling to room temperature, the sodium chloride that has precipitated is filtered off and the ethanol is removed in a rotary evaporator. Subsequent filtration yields 256.1 g of light-yellow bis(3-[triethoxysilyl]propyl)tetrasulfane having an iodine colour value of from 5 to 7 mg of iodine/100 ml.

$^1$H-NMR (CDCl$_3$): δ 0.75 (m, 6 H, Si—(C$\underline{H}_2$)—(CH$_2$)—(CH$_2$)—S), 1.22 (t, $^3$J(HH)=14 Hz, 18 H, Si—O—CH$_2$—C$\underline{H}_3$), 1.72–1.95 (m, 6 H, Si—(CH$_2$)—(C$\underline{H}_2$)—(CH$_2$)—S), 2.65–3.06 (m, Si—(CH$_2$)—(CH$_2$)—(C$\underline{H}_2$)—S), 3.82 (q, $^3$J(HH)=14 Hz, 12 H, Si—O—C$\underline{H}_2$—CH$_3$).

Example 2

2.4 g of chloropropyltrichlorosilane are added dropwise at room temperature to 240.8 g of chloropropyltriethoxysilane (neutral). Stirring is then carried out for one hour at 80° C. After addition of 200 ml of ethanol, the temperature falls to 62° C., 87.1 g of sodium polysulfide are added and the reaction mixture is boiled at reflux for 1.5 hours at 82° C., with stirring. After cooling to room temperature, the sodium chloride that has precipitated is filtered off and the ethanol is removed in a rotary evaporator. Subsequent filtration yields 257.3 g of light-yellow bis(3-[triethoxysilyl]propyl) tetrasulfane having an iodine colour value of from 7 to 10 mg of iodine/100 ml.

$^1$H-NMR (CDCl$_3$): δ 0.75 (m, 6 H, Si—(CH$_2$)—(CH$_2$)—(CH$_2$)—S), 1.22 (t, $^3$J(HH)=14 Hz, 18 H, Si—O—CH$_2$—CH$_3$), 1.72–1.95 (m, 6 H, Si—(CH$_2$)—(CH$_2$)—(CH$_2$)—S), 2.65–3.06 (m, Si—(CH$_2$)—(CH$_2$)—(CH$_2$)—S), 3.82 (q, $^3$J(HH)=14 Hz, 12 H, Si—O—CH$_2$—CH$_3$).

Example 3

11.4 kg of chloropropyltrichlorosilane are added at room temperature to a solution of 1122 kg of chloropropyltriethoxysilane (neutral) in 950 kg of ethanol. Stirring is then carried out for 30 minutes at room temperature. 390 kg of sodium polysulfide are then added and the reaction mixture is boiled at reflux for one hour at 82° C., with stirring. After cooling to room temperature, the sodium chloride that has precipitated is filtered off and the ethanol is removed in vacuo. Subsequent filtration yields 1250 kg of light-yellow bis(3-(triethoxysilyl]propyl)tetrasulfane having an iodine colour value of from 5 to 7 mg of iodine/100 ml.

$^1$H-NMR (CDCl$_3$): δ 0.75 (m, 6 H, Si—(CH$_2$)—(CH$_2$)—(CH$_2$)—S), 1.22 (t, $^3$J(HH)=14 Hz, 18 H, Si—O—CH$_2$—CH$_3$), 1.72–1.95 (m, 6 H, Si—(CH$_2$)—(CH$_2$)—(CH$_2$)—S), 2.65–3.06 (m, Si—(CH$_2$)—(CH$_2$)—(CH$_2$)—S), 3.82 (q, $^3$J(HH)=14 Hz, 12 H, Si—O—CH$_2$—CH$_3$).

Example 4

4.8 g of chloropropyltrichlorosilane are added dropwise at room temperature to a solution of 481.6 g of chloropropyltriethoxysilane (neutral) in 450 ml of ethanol. Boiling at reflux is then carried out for one hour at 80° C., with stirring. After cooling to 58° C., 89.8 g of sodium sulfide and 105.8 g of sulfur are added and the reaction mixture is boiled at reflux for 1.5 hours at 82° C., with stirring. After cooling to room temperature, the sodium chloride that has precipitated is filtered off and the ethanol is removed in a rotary evaporator. Subsequent filtration yields 500.4 g of light-yellow bis(3-[triethoxysilyl]propyl)tetrasulfane having an iodine colour value of from 5 to 7 mg of iodine/100 ml) (sic).

$^1$H-NMR (CDCl$_3$): δ 0.75 (m, 6 H, Si—(CH$_2$)—(CH$_2$)—(CH$_2$)—S), 1.22 (t, $^3$J(HH)=14 Hz, 18 H, Si—O—CH$_2$—CH$_3$), 1.72–1.95 (m, 6 H, Si—(CH$_2$)—(CH$_2$)—(CH$_2$)—S), 2.65–3.06 (m, Si—(CH$_2$)—(CH$_2$)—(CH$_2$)—S), 3.82 (q, $^3$J(HH)=14 Hz, 12 H, Si—O—CH$_2$—CH$_3$).

Example 5
(Comparison Example 1):

87.1 g of sodium polysulfide are added at 60° C. to a solution of 240.8 g of chloropropyltriethoxysilane (neutral) in 200 ml of ethanol, and the reaction mixture is boiled at reflux for 1.5 hours at 82° C., with stirring. After cooling to room temperature, the sodium chloride that has precipitated is filtered off and the ethanol is removed in a rotary evaporator. Subsequent filtration yields 255.0 g of red bis(3-[triethoxysilyl]propyl)tetrasulfane having an iodine colour value of >20 mg of iodine/100 ml.

$^1$H-NMR (CDCl$_3$): δ 0.75 (m, 6 H, Si—(CH$_2$)—(CH$_2$)—(CH$_2$)—S), 1.22 (t, $^3$J(HH)=14 Hz, 18 H, Si—O—CH$_2$—CH$_3$), 1.72–1.95 (m, 6 H, Si—(CH$_2$)—(CH$_2$)—(CH$_2$)—S), 2.65–3.06 (m, Si—(CH$_2$)—(CH$_2$)—(CH$_2$)—S), 3.82 (q, $^3$J(HH)=14 Hz, 12 H, Si—O—CH$_2$—CH$_3$).

Example 6
(Comparison Example 2):

240.8 g of chloropropyltriethoxysilane (neutral) are placed at room temperature in 200 ml of ethanol. 30 ml of a 1-molar ethanolic HCl solution are then added, and stirring is carried out for 30 minutes at RT. After addition of 87.1 g of sodium polysulfide, the reaction mixture is boiled at reflux for 1.5 hours at 82° C., with stirring. After cooling to room temperature, the sodium chloride that has precipitated is filtered off and the ethanol is removed in a rotary evaporator. Subsequent filtration yields 253.5 g of red bis(3-[triethoxysilyl]propyl)tetrasulfane having an iodine colour value of >20 mg of iodine/100 ml.

Example 7
(Comparison Example 3):

89.8 g of sodium sulfide and 105.8 g of sulfur are added at 60° C. to a solution of 481.6 g of chloropropyltriethoxysilane (neutral) in 450 ml of ethanol, and the reaction mixture is boiled at reflux for 1.5 hours at 82° C., with stirring. After cooling to room temperature, the sodium chloride that has precipitated is filtered off and the ethanol is removed in a rotary evaporator. Subsequent filtration yields 496.3 g of red bis(3-[triethoxysilyl]propyl)tetrasulfane having an iodine colour value of >20 mg of iodine/100 ml.

$^1$H-NMR (CDCl$_3$): δ 0.75 (m, 6 H, Si—(CH$_2$)—(CH$_2$)—(CH$_2$)—S), 1.22 (t, $^3$J(HH)=14 Hz, 18 H, Si—O—CH$_2$—CH$_3$), 1.72–1.95 (m, 6 H, Si—(CH$_2$)—(CH$_2$)—(CH$_2$)—S), 2.65–3.06 (m, Si—(CH$_2$)—(CH$_2$)—(CH$_2$)—S), 3.82 (q, $^3$J(HH)=14 Hz, 12 H, Si—O—CH$_2$—CH$_3$).

Example 8

5 ml of chloropropyltrichlorosilane are added dropwise at room temperature to 20 ml of chloropropyltriethoxysilane (neutral). Stirring is then carried out for one hour at 80° C. After cooling to room temperature, GC-MS spectra of the resulting reaction mixture and, for control purposes, of the chloropropyltriethoxysilane (neutral) that has been used are recorded (FIGS. 1 and 2). The addition of chloropropyltrichlorosilane to neutral chloropropyltriethoxysilane leads to the formation of chloropropylmonochlorodiethoxysilane and chloropropyldichloromonoethoxysilane.

GC: HP 5890 II; MS: Finnigan MAT 95; column: 30 m×0.25 mm DB-5MS; df: 0.25 μm U026; helium: 80 kPa; temp.: 50(5)-5-100-15-300(10); split: 100 ml/min; inj.vol.: 0.1 μl dissolved in n-hexane.

The iodine colour value is determined according to Din 6162.

What is claimed is:

1. Process for the preparation of yellow bis(3-[triethoxysilyl]propyl)tetrasulfane having an iodine colour value of ≦10 mg of iodine/100 ml, characterised in that chloropropyltrichlorosilane is added to neutral chloropropyltriethoxysilane and reaction with sodium polysulfide or with Na$_2$S and sulfur in ethanol is then carried out.

2. Process according to claim 1, characterised in that chloropropyltrichlorosilane is added in an amount of from 0.1 to 20 wt. %.

3. Process according to claim 1, characterised in that the reaction mixture is heated to from 20 to 90° C. before the addition of sodium polysulfide or of Na$_2$S and sulfur.

* * * * *